(12) United States Patent
Poly et al.

(10) Patent No.: US 8,530,166 B2
(45) Date of Patent: Sep. 10, 2013

(54) **MULTIPLEX AMPLIFICATION REACTION METHOD FOR DETERMINATION OF *CAMPYLOBACTER JEJUNI* PENNER/CAPSULE TYPE**

(75) Inventors: Frederic Poly, Silver Spring, MD (US); Patricia Guerry, Silver Spring, MD (US); Carl Mason, Nonthaburi (TH); Oralak Serichantalergs, Bankok (TH)

(73) Assignee: The United States of America, as represented by the Secretary of the Navy, Washington, DC (US)

( * ) Notice: Subject to any disclaimer, the term of this patent is extended or adjusted under 35 U.S.C. 154(b) by 198 days.

(21) Appl. No.: 13/031,718

(22) Filed: Feb. 22, 2011

(65) Prior Publication Data

US 2011/0207138 A1 Aug. 25, 2011

Related U.S. Application Data

(60) Provisional application No. 61/307,632, filed on Feb. 24, 2010.

(51) Int. Cl.
*C12Q 1/68* (2006.01)
*C12P 19/34* (2006.01)

(52) U.S. Cl.
USPC ............................ 435/6.12; 435/6.1; 435/6.11

(58) Field of Classification Search
None
See application file for complete search history.

(56) References Cited

U.S. PATENT DOCUMENTS

| 2006/0051752 A1 | 3/2006 | Wang et al. |
| 2008/0038742 A1 | 2/2008 | Porter et al. |

OTHER PUBLICATIONS

Karlyshev et al. Analysis of *Campylobacter jejuni* capsular loci reveals multiple mechanisms for the generation of structural diversity and the ability to form complex heptoses. Mol Microbiol. 2005, vol. 55(1), p. 90-103. Abstract; p. 91, col. 1, para 2; p. 92, Fig 1 and Table 1; and p. 100, col. 2, para 2 and 4. Relevant to Claims 1-20.

Genbank_AL111168, *Campylobacter jejuni* subsp. *jejuni* NCTC 11168 complete genome, May 13, 2009, [online]. [Retrieved on Apr. 7, 2011]. Retrieved from the Internet: <URL: http://www.ncbi.nlm.nih.gov/nuccore/AL111168> Entire document, especially Definition; and complement(1373947..1374810)/locus_tag="Cj1437c" Relevant to Claims 4, 10, 13, 16-17.

Genbank_BX545859, *Campylobacter jejuni*, Apr. 17, 2005, [online]. [Retrieved on Apr. 6, 2011]. Retrieved from the Internet: <URL: http://www.ncbi.nlm.nih.gov/nuccore/BX545859> Entire document, especially Definition; and gene complement (9304..11844)/locus_tag="HS1.08" Relevant to Claims 13,17.

McNally et al. Commonality and Biosynthesis of teh o-Methyl Phosphoramidate Capsule Modification in *Campylobacter jejuni*. J Biol Chem. 2007, vol. 282(39), p. 28566-76. Abstract. Relevant to Claims 1-20.

Poly et al. Discrimination of major capsular types of *Campylobacter jejuni* by multiplex PCR.J Clin Microbiol. Mar. 16, 2011. [Epub ahead of print] PDF file: p. 1-31, Entire document. Relevant to Claims 1-20.

Rachlin, et al., MuPlex: multi-objective multiplex PCR assay design. Nucleic Acids Research, 2005, vol. 33: W544-W547. Relevant to Claims 1-20.

Vallone and Butler, AutoDimer: a screening tool for primer-dimer and hairpin structures, Biotechniques, 2004, vol. 37: 226-231. Relevant to Claims 1-20.

*Primary Examiner* — Young J Kim
(74) *Attorney, Agent, or Firm* — Albert M. Churillo; Joseph K. Hemby; Ning Yang (57) ABSTRACT

The inventive method and associated reagents relate to a molecular approach to determining *Campylobacter jejuni* capsule/Penner types. The invention also relates to a method of identifying *Campylobacter jejuni* types using the inventive primers in a multiplex PCR assay.

13 Claims, 2 Drawing Sheets

FIG 1

Percentage of total identified strains

FIG. 2

SEQUENCE LISTING

<160> NUMBER OF SEQ ID NOS: 42

<210> SEQ ID NO 1
<211> LENGTH: 25
<212> TYPE: DNA
<213> ORGANISM: Campylobacter jejuni

<400> SEQUENCE: 1
cagcattgga ggatttacaa tatat                                              25

<210> SEQ ID NO 2
<211> LENGTH: 22
<212> TYPE: DNA
<213> ORGANISM: Campylobacter jejuni

<400> SEQUENCE: 2
catcctagca caactcactt ca                                                 22

<210> SEQ ID NO 3
<211> LENGTH: 24
<212> TYPE: DNA
<213> ORGANISM: Campylobacter jejuni

<400> SEQUENCE: 3
ggtaaggttg attctgggtt taat                                               24

<210> SEQ ID NO 4
<211> LENGTH: 22
<212> TYPE: DNA
<213> ORGANISM: Campylobacter jejuni

<400> SEQUENCE: 4
agattaggcc aagcaatgat aa                                                 22

<210> SEQ ID NO 5
<211> LENGTH: 20
<212> TYPE: DNA
<213> ORGANISM: Campylobacter jejuni

<400> SEQUENCE: 5
tatatttggt tagggatcca                                                    20

<210> SEQ ID NO 6
<211> LENGTH: 23
<212> TYPE: DNA
<213> ORGANISM: Campylobacter jejuni

<400> SEQUENCE: 6
cctaacatat catacactac ggt                                                23

<210> SEQ ID NO 7
<211> LENGTH: 26
<212> TYPE: DNA
<213> ORGANISM: Campylobacter jejuni

<400> SEQUENCE: 7
catacatttg ctttcagatt ctttac                                             26

<210> SEQ ID NO 8
<211> LENGTH: 21
<212> TYPE: DNA
<213> ORGANISM: Campylobacter jejuni

```
<400> SEQUENCE: 8
acacgcctat tgttgttgtt c                                              21

<210> SEQ ID NO 9
<211> LENGTH: 19
<212> TYPE: DNA
<213> ORGANISM: Campylobacter jejuni

<400> SEQUENCE: 9
tcttatgcag cacgctgat                                                 19

<210> SEQ ID NO 10
<211> LENGTH: 22
<212> TYPE: DNA
<213> ORGANISM: Campylobacter jejuni

<400> SEQUENCE: 10
caaattcaat cgactagcca ct                                             22

<210> SEQ ID NO 11
<211> LENGTH: 24
<212> TYPE: DNA
<213> ORGANISM: Campylobacter jejuni

<400> SEQUENCE: 11
acaggtaata aaatgtgcga gttt                                           24

<210> SEQ ID NO 12
<211> LENGTH: 20
<212> TYPE: DNA
<213> ORGANISM: Campylobacter jejuni

<400> SEQUENCE: 12
atgcatctgc aacatcatcc                                                20

<210> SEQ ID NO 13
<211> LENGTH: 27
<212> TYPE: DNA
<213> ORGANISM: Campylobacter jejuni

<400> SEQUENCE: 13
cttacatatg ctggtagaga tgatatg                                        27

<210> SEQ ID NO 14
<211> LENGTH: 20
<212> TYPE: DNA
<213> ORGANISM: Campylobacter jejuni

<400> SEQUENCE: 14
tgcaatctct aaagcccaag                                                20

<210> SEQ ID NO 15
<211> LENGTH: 19
<212> TYPE: DNA
<213> ORGANISM: Campylobacter jejuni

<400> SEQUENCE: 15
aggcaagcag gaattgttt                                                 19

<210> SEQ ID NO 16
<211> LENGTH: 22
<212> TYPE: DNA
<213> ORGANISM: Campylobacter jejuni
```

<400> SEQUENCE: 16
ttaattgctc tttggcaatc tt                                          22

<210> SEQ ID NO 17
<211> LENGTH: 21
<212> TYPE: DNA
<213> ORGANISM: Campylobacter jejuni

<400> SEQUENCE: 17
ttggcggtaa gttttttgaag a                                          21

<210> SEQ ID NO 18
<211> LENGTH: 21
<212> TYPE: DNA
<213> ORGANISM: Campylobacter jejuni

<400> SEQUENCE: 18
gcaagagaaa catctcgcct a                                           21

<210> SEQ ID NO 19
<211> LENGTH: 20
<212> TYPE: DNA
<213> ORGANISM: Campylobacter jejuni

<400> SEQUENCE: 19
ttcacgtgga ggattattgg                                             20

<210> SEQ ID NO 20
<211> LENGTH: 25
<212> TYPE: DNA
<213> ORGANISM: Campylobacter jejuni

<400> SEQUENCE: 20
ttgaacattt catgtgtatt cccta                                       25

<210> SEQ ID NO 21
<211> LENGTH: 20
<212> TYPE: DNA
<213> ORGANISM: Campylobacter jejuni

<400> SEQUENCE: 21
gtggacatgg aactgggact                                             20

<210> SEQ ID NO 22
<211> LENGTH: 23
<212> TYPE: DNA
<213> ORGANISM: Campylobacter jejuni

<400> SEQUENCE: 22
aaaacgttta aagtcagtgg aaa                                         23

<210> SEQ ID NO 23
<211> LENGTH: 24
<212> TYPE: DNA
<213> ORGANISM: Campylobacter jejuni

<400> SEQUENCE: 23
gcttgggaga tgaatttacc ttta                                        24

<210> SEQ ID NO 24
<211> LENGTH: 27
<212> TYPE: DNA
<213> ORGANISM: Campylobacter jejuni

```
<400> SEQUENCE: 24
gctttatatc tatccagtcc attatca                                          27

<210> SEQ ID NO 25
<211> LENGTH: 20
<212> TYPE: DNA
<213> ORGANISM: Campylobacter jejuni

<400> SEQUENCE: 25
atggtaaaac cggcatttca                                                  20

<210> SEQ ID NO 26
<211> LENGTH: 20
<212> TYPE: DNA
<213> ORGANISM: Campylobacter jejuni

<400> SEQUENCE: 26
atgcttcagt tccacccaaa                                                  20

<210> SEQ ID NO 27
<211> LENGTH: 21
<212> TYPE: DNA
<213> ORGANISM: Campylobacter jejuni

<400> SEQUENCE: 27
agaagatgca ctaggctcta g                                                21

<210> SEQ ID NO 28
<211> LENGTH: 20
<212> TYPE: DNA
<213> ORGANISM: Campylobacter jejuni

<400> SEQUENCE: 28
gctatctaat tccatccctg                                                  20

<210> SEQ ID NO 29
<211> LENGTH: 62
<212> TYPE: DNA
<213> ORGANISM: Campylobacter jejuni

<400> SEQUENCE: 29
cagcattgga ggatttacaa tatatgagag attatgtaga tgaagtgagt tgtgctagga      60
tg                                                                     62

<210> SEQ ID NO 30
<211> LENGTH: 149
<212> TYPE: DNA
<213> ORGANISM: Campylobacter jejuni

<400> SEQUENCE: 30
agattaggcc aagcaatgat aataaattct aaaaattttt taggttatat attttttaccg     60 tatatttat taagtattgt tatactatat aaacaagagc aaaaaaatta taaacataaa      120
attaaattaa acccagaatc aaccttacc                                       149

<210> SEQ ID NO 31
<211> LENGTH: 370
<212> TYPE: DNA
<213> ORGANISM: Campylobacter jejuni

<400> SEQUENCE: 31
tatatttggt tagggatcca atttcgagat taaaaacggg tttaaatcat attaatttaa      60
```

```
aggcgaatag acttgatcgt tttgatttgg atacacctat agaaagagtt ttagatagag      120
agacatatta tttcgaatct cctttgccaa cctgtgatca tataaaaact tattggattt      180
atgcggaaag ctttttaga ttaaattttt taacacaatt ttttaaaata gaaaaaatta       240
```
(Note: the line above should read:)
```
atgcggaaag cttttttaga ttaaattttt taacacaatt ttttaaaata gaaaaaatta      240
cttacttaga catggctagt attaaacctg aatatgctta tcatactttc agtcaattaa      300
atgctttata ccattttaga caaatatcaa aaaatttatt ccataatacc gtagtgtatg      360
atatgttagg                                                             370

<210> SEQ ID NO 32
<211> LENGTH: 185
<212> TYPE: DNA
<213> ORGANISM: Campylobacter jejuni

<400> SEQUENCE: 32
acacgcctat tgttgttgtt cctactagct ttaatgaaat caaagccagt gatttggcta      60
catatggagc taatataatt atatatgcta atcatatgct tcgtgcttct tttgttgcaa      120
tgcaaaatgt ggcaaaagaa attttggaaa atgatagaag taaagaatct gaaagcaaat      180
gtatg                                                                  185

<210> SEQ ID NO 33
<211> LENGTH: 229
<212> TYPE: DNA
<213> ORGANISM: Campylobacter jejuni

<400> SEQUENCE: 33
tcttatgcag cacgctgata ttttatatgg ctccaatgaa tctatgttta gagcattggc      60
tgcaaatatt tcttatcgaa atattcagaa taaccttgtt gatcatgttt ttgatttgca      120
atctcaatat gaaataatta gctcaaatat tgataattat aatattgata atttatataa      180
aagtgcatct tgtatttatt tatttatagt ggctagtcga ttgaatttg                  229

<210> SEQ ID NO 34
<211> LENGTH: 325
<212> TYPE: DNA
<213> ORGANISM: Campylobacter jejuni

<400> SEQUENCE: 34
acaggtaata aaatgtgcga gttttataac cagcaatttg gcacaaattt tattactta      60 gttccaacaa gtatttatgg acctggggat aattttaatt tagccacagc tcatgttttt      120
cctgcaatat ttgcaaaaat ttatttagga aaattgctaa atgagcaaaa gcatcaagag      180
ttgtttaata gcttgagatt ggataatata caagatgttt taaaatattt aagtcaattt      240
gatattgatg agaataaggt tacattgctt ggaagtggta accctagaag agaatttatt      300
tacgtggatg atgttgcaga tgcat                                            325

<210> SEQ ID NO 35
<211> LENGTH: 279
<212> TYPE: DNA
<213> ORGANISM: Campylobacter jejuni

<400> SEQUENCE: 35
cttacatatg ctggtagaga tgatatgtta ttaaaaattg aagaagttgt tttaaaacat      60
ccaaaactgt ataaatataa aaatttttata aaaaaatttt atcaaaaaga gggttttat     120 ccttttaata tgtttattat gaaaaaaaat ctttttttg aatatgcgga atttatattt      180
actattttta atgaaatatg gagtgatgat attgagaata gttaaaaatt aagaggttta      240
```

```
cattatcaaa gagaattagc ttgggctttta gagattgca                  279

<210> SEQ ID NO 36
<211> LENGTH: 251
<212> TYPE: DNA
<213> ORGANISM: Campylobacter jejuni

<400> SEQUENCE: 36
aggcaagcag gaattgtttt atattaaaga aggttttgat ctaagatatt atttattgca   60
aaagatgtat gatattaata ccagtggttc taaaatatat catagtttat ttattgatga  120
actacaagat caattaaaaa atggaaatat aaaaagtgag gtaaaatttg caatttgtat  180
gtatggtatg ttgcgtggtg attggaaggg aacgttagaa aaaaatataa agattgccaa  240
agagcaatta a                                                       251

<210> SEQ ID NO 37
<211> LENGTH: 607
<212> TYPE: DNA
<213> ORGANISM: Campylobacter jejuni

<400> SEQUENCE: 37
ttggcggtaa gttttgaag aaatgccctg atgagttaaa aactctttct ttttaaagc     60 agaaatttcc aaatacttat agcaaattaa atatagagca aggtgttcaa aaataaacc   120 aaaaatatat tcaggatata gtaaagtgct ctaatattca aattcaaaat gaagaagaat  180
ttattagctc tttgtattta aatatgacat ctaaaagaga aacaaatcga ataaaaatgt  240
tttatggaat ttataaatct atacagatgg cgttagaata tgaaaaaata aataaattta  300
ggtatgatta tatttttaga gtaaggccag atatcggttt aatagggaat attgagataa  360
aagatttaaa taagcttaaa aataatgagc ttgctgtaga tttttttctt tatggtgtgc  420
aagatcaatt tttttatgca catagaaatg ttatgattga agtcgcaaaa atatgggaat  480
attgttatga aaaaaatgat attttttttaa gaagttttga tagttctcat tatttattat  540
tcatctattt aactttgaga aatattttga cagttaaacc taattttagg cgagatgttt  600
ctcttgc                                                            607

<210> SEQ ID NO 38
<211> LENGTH: 342
<212> TYPE: DNA
<213> ORGANISM: Campylobacter jejuni

<400> SEQUENCE: 38
ttcacgtgga ggattattgg taaatcctga tattgatagt ttgtcaaaag ctatgataaa   60
atatttaaaa gaatctattc aaacttgtaa ttttgacttt gtcgagtata ataatattat  120
tttagaaaaa tttaattatc ttttttggagt tagtttcgaa gggtataaaa atgacaggtg  180
tatattgtct ccatgtatca ttatggcaaa gcctgatggc tttggtatga gactgtttgc  240
gatgatggca gggttattgt tatccgaaaa aactaatttg ccattttatt ttaaatgggg  300
aaagattgaa gatgtgatag ggaatacaca tgaaatgttc aa                     342

<210> SEQ ID NO 39
<211> LENGTH: 652
<212> TYPE: DNA
<213> ORGANISM: Campylobacter jejuni

<400> SEQUENCE: 39
gtggacatgg aactgggact gaagcattaa aagtattttt atcttacaat aaaattatta   60
```

```
ttccggataa ttttttttaat tatgaaacag gattacaaag atataaatat gctcttaata    120
tcttattaaa tgatattgat catataaaag gcatacgctt aaaagattat cattttaatg    180
attttgaaaa attttgtaaa ttgattcaaa aaaaatgtaa attattttt caagtaagag     240 attattttga atatttact tgctatataa atcatagaac tagaaaatct gacgcaatta    300
tgaattttga tctacaaact aatttaagtg atgttttcga tcgttttat tatttttcga     360 gcggagaaaa tcatccaatt agattaaatc taaaaaattt tttatcttgg cctgcattac    420
atcaagaaat gggatttaga acttgtgtaa tggagtattc gatgctacaa aattttgata    480
atattttaga tgttctttat attgatataa aagatattat aggagtagac acaaaaaaca    540
caattcaaaa aatatgtaat tttataaata tatcttataa tcaagaatat aattattctg    600
aaaatattat aggagattta aaaattatat ttccactgac tttaaacgtt tt            652

<210> SEQ ID NO 40
<211> LENGTH: 161
<212> TYPE: DNA
<213> ORGANISM: Campylobacter jejuni

<400> SEQUENCE: 40
gcttgggaga tgaatttacc tttacctgat gggtataagt ttgttttaat aggaggccat     60
ggaacaggag agaaagcttt tcaagaaatg ctttccagat gtaatgttaa aattttagaa    120
aaaaatattt ggtatgataa tggactggat agatataaag c                        161

<210> SEQ ID NO 41
<211> LENGTH: 441
<212> TYPE: DNA
<213> ORGANISM: Campylobacter jejuni

<400> SEQUENCE: 41
atgcttcagt tccacccaaa ttaatccatt ctttatggtt gtcataccat tcatcatacg     60
cacttcctag ataaactttc caaggtttat tatatcccaa taaatgaatt aattttgcat    120
tatttttatt ttcataagag aatacatgat atatatcttt tggaaaaata tcaactttta    180
aatcaaattt ctcaatcatc atttgcaata taccttgctc agcatatttt agttttgaag    240
aatattgttc taattttga tatagatatt ttcttatttc caaaggattc tttaatgcat    300
cagagaatat aattaaacct gaagcataag cagtggcatt catatcgatt tcatcgattt    360
cgtcgataaa aaaatctctt atagagtgat tggtcggata aggatataga tctaaagaca    420
ttgaaatgcc ggttttacca t                                              441

<210> SEQ ID NO 42
<211> LENGTH: 148
<212> TYPE: DNA
<213> ORGANISM: Campylobacter jejuni

<400> SEQUENCE: 42
agaagatgca ctaggctcta gaatgtatgc ttttgttaat ggaatggtta ttgcaagaaa     60
aataggtttt gatttggat atgtttggaa agagattaat catgattttc aaaaaaatga    120
tgatttagca gggatggaat tagatagc                                       148
```

MULTIPLEX AMPLIFICATION REACTION METHOD FOR DETERMINATION OF CAMPYLOBACTER JEJUNI PENNER/CAPSULE TYPE

CROSS-REFERENCES TO RELATED APPLICATIONS

This application claims the benefit of U.S. Provisional Application No. 61/307,632, filed 24 Feb. 2010, which is incorporated by reference, herein.

BACKGROUND OF INVENTION

1. Field of Invention

The inventive subject matter relates to a molecular method for determining *Campylobacter jejuni* capsule/Penner types.

2. Background

*Campylobacter* is a major cause of human bacterial diarrheal disease worldwide, with *C. jejuni*, and to a lesser extent *C. coli*, the most important pathogenic *Campylobacter* species. Campylobacteriosis symptoms range from asymptomatic infection to bloody diarrhea associated with abdominal pain and fever. The major source of human infection is through consumption of uncooked poultry, which is commonly colonized by *C. jejuni*. Post infectious sequelae associated with *C. jejuni* include reactive arthritis, Guillain-Barré syndrome and irritable bowel syndrome.

The molecular pathogenesis of *C. jejuni* is not well understood, but a polysaccharide capsule (CPS) is one of the few recognized virulence determinants of this pathogen. The capsular polysaccharide undergoes a reversible phase variation in expression (Bacon, et al., Mol. Microbiol. 40:769-777 (2001)). The capsule contributes to serum resistance of *C. jejuni*, the ability of *C. jejuni* to invade intestinal epithelial cells in vitro, and, in a ferret model, is required for virulence (Bacon, et al., Mol. Microbiol. 40:769-777 (2001)). More recently, polysaccharide capsule conjugated to a protein carrier has been shown to protect non-human primates against diarrheal disease Monteiro, et al., Infect Imm. 77(3): 1128-36 (2009). Differentiation of *Campylobacter jejuni* strains is typically conducted through the use of Penner serotyping.

The Penner or "heat stable" serotyping scheme is a passive slide hemaglutination assay for both *C. jejuni* and *C. coli* that includes 47 *C. jejuni* serotypes. Rabbit polyclonal antibodies are generated against whole cells of each of the 47 type strains. Antigens are extracted from *C. jejuni* strains to be tested by heating bacterial suspensions in saline at 100° C. These "heat-stable" antigens are used to sensitize sheep erythrocytes, which are used in a passive slide hemagglutination assay with the specific polyclonal antisera. Genetic studies indicate that CPS is the major serodeterminant of the Penner scheme. Thus, mutation of genes required for CPS biogenesis rendered many strains untypable in the Penner scheme.

Figure 1:
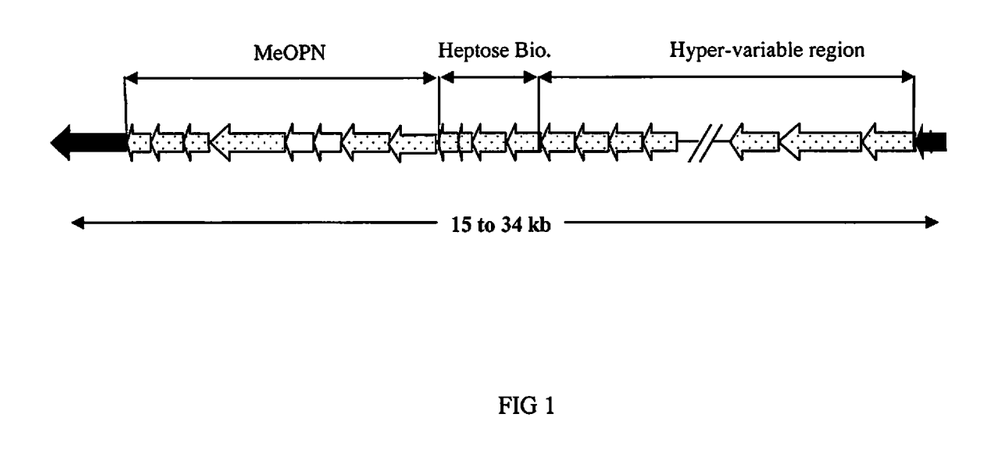
FIG. 1. Schematic of the general organization of the capsule loci of C. jejuni. The region between kpsC and kpsF (black arrows) encodes the genes for synthesis of distinct capsule structures. If present, genes for heptose and MeOPN synthesis are highly conserved. The region to the right is the hyper-variable region containing sugar transferases and sugar biosynthetic genes.

However, other surface heat stable surface structures such as lipooligosaccharides (LOS) may also contribute to serospecificity of some Penner types. The capsular polysaccharides of *C. jejuni* are known to be structurally diverse (Karlyshev et al., *Molecular Microbiology* 55:90-103). This structural diversity is consistent with the variability observed in the genes encoding the capsule in *C. jejuni*. The capsule locus of *C. jejuni* includes both highly conserved genes involved in capsule synthesis and highly variable loci that encode genes involved in synthesis of specific sugars and specific glycosyl transferases required to link the sugars together. The variable CPS locus located between two conserved genes, kpsC and kpsF, and the variable genes can range from 15 to 34 kb (FIG. 1). Variable genes also encode synthesis and transfer of modifications to the sugars, such as methyl phosphormidate (MeOPN) (Karlyshev et al., *Molecular Microbiology* 55:90-103).

Penner serotyping is technically difficult to perform and expensive to produce the type antisera. As a result, only a handful of reference laboratories routinely perform Penner typing. Moreover, many serotypes fall into Penner "complexes". The significance of these complexes is not totally understood in most cases, but they appear to include capsules with related structures (Aspinall et al. *Carbohydr Res.* 231: 13-30 (1992).

Others have tried to replace the laborious Penner serotyping using a molecular typing approach involving restriction fragment length polymorphism (RFLP) analysis of PCR amplified lipooligosaccharide (LOS) loci (Shi et al. *J Clin Microbiol.* 40(5):1791-7 (2002); Nakari et al., *J Clin Microbiol.* 43(3):1166-70) (2005). However, these RFLP methods have not been widely used and have not replaced Penner serotyping as the typing method of choice. This may be due in part to the RFLP method requiring amplification of a 9.6 kb fragment. Using PCR to generate such large amplicons is difficult and can place special requirements on the PCR conditions and reagents used, as demonstrated by Nakari et al., who were unable to generate amplified fragments using the amplification conditions described by Shi et al. These RFLP methods are also limited because they are based on the amplification of the LOS locus. At the time of the Shi et al. study, it was known that both the LOS and CPS structure were part of the Heat Stable antigen (HS) recognized through the Penner serotyping method. However, in 2005, CPS was demonstrated to be the major serodeterminant of the Penner method (Karylshev, et al., Mol. Micro. 55: 90-103 (2005). This helps explain why Shi et al. and Nakari et al. found only partial correlation between the Penner serotypes and RFLP groups. Penner serotyping distinguishes strains that cannot be distinguished by this RFLP method. For example, the most common RFLP type, Hh1Dd1, contained strains belonging to several HS serotypes, including HS 6,7, HS12, HS 27, HS 55, HS 21, HS10, HS 57, HS 6, HS 15, HS 23,36,53, and HS 27+HS 31 (Nakari et al., *J Clin Microbiol.* 43(3):1166-70 (2005)). And some serotypes, such as HS 2, HS 3, HS 4 complex, HS 8, HS10, HS11, HS12, HS15, HS19, HS 31, HS 32, HS 41, HS 57, and HS 23,36,53 include more than one RFLP (Nakari et al., *J Clin Microbiol.* 43(3):1166-70 (2005).

SUMMARY OF THE INVENTION

The current invention relates to reagents and method to identify *Campylobacter jejuni* Capsule/Penner types via molecular, rather than serological, methods.

Therefore, an object of the invention is a panel of multiplex DNA primers for identification of *C. jejuni* Capsule/Penner types by polymerase chain reaction (PCR).

Several important advantages of amplification reactions over serological determination are evident. First, it is technically difficult to perform and expensive to produce type antisera. As a result, few reference laboratories are capable of routine Penner typing. Additionally, many serotypes fall into Penner "complexes."

Amplification methods, unlike typing sera methods, are relatively available to research and reference laboratories. Furthermore, no expression of capsule is needed. Therefore, there are no affects due to phase variation in capsule expression, as is possible with serotyping. Multiplexing reduces the number of reactions to be performed per samples. Additionally, amplification reactions do not suffer from CPS being shut down or modified thru slipstrand mutations. The instant invention can identify 14 CPS types, that include 17 serotypes.

The multiplex amplification technique amplifies a fragment less than 1 kb that can be routinely performed in any molecular biology lab worldwide.

DETAILED DESCRIPTION OF PREFERRED EMBODIMENTS

The following terms are defined:

"Amplification reaction" refers to a method of detecting target nucleic acid by in vitro amplification of DNA or RNA.

"Polymerase chain reaction (PCR)" refers to the amplification of a specific DNA sequence, termed target or template sequence, that is present in a mixture, by adding two or more short oligonucleotides, also called primers, that are specific for the terminal or outer limits of the template sequence. The template-primers mixture is subjected to repeated cycles of heating to separate (melt) the double-stranded DNA and cooling in the presence of nucleotides and DNA polymerase such that the template sequence is copied at each cycle.

"Primer" refers to DNA oligonucleotides complementary to a region of DNA and serves as the initiation of amplification reaction from the 5' to 3' direction.

"Primer pair refers to the forward and reverse primers in an amplification reaction leading to amplification of a double-stranded DNA region of the target.

"Target" refers to a nucleic acid region bound by a primer pair that is amplified through an amplification reaction.

The term "multiplex amplification reaction" herein refers the detection of more than one template in a mixture by the addition of more than one set of oligonucleotide primers.

The term "capsule" herein refers to the structure lying outside the cell wall of bacteria, such as Campylobacter jejuni.

Utilizing genomic and capsule loci sequences, a molecular method for determining Penner and capsule type was developed. This method is simpler than Penner typing. The inventive method is more easily standardized than Penner serotyping, since molecular reagents (i.e., primers) can be produced and standardized resulting in lower cost. Additionally, the method does not require that the capsule be expressed. Therefore, it is not affected by phase variation in capsule expression, unlike the typing system.

In one embodiment, the current invention provides a method to specifically recognize Capsule/Penner types thru PCR amplification of type specific sequences. The inventive method and reagents permit identification of Campylobacter jejuni Penner types without the potential for capsule shutdown or modification due to slipstrand mutations.

EXAMPLE 1

Design of Primer Sequences Correlating with Penner Serotype

The capsule locus of C. jejuni includes both highly conserved genes involved in capsule synthesis and highly variable loci that encode genes involved in synthesis of specific sugars and specific glycosyl transferases required to link the sugars together. The variable CPS locus, located between two conserved genes, kpsC and kpsF, and the variable genes range from 15 to 34 kb (FIG. 1). Variable genes also encode synthesis and transfer of modifications to the sugars, such as methyl phosphormidate (Karlyshev, A. et al., Mol. Microbiol. 55:90-103 (2005)). In a preferred embodiment, based on the DNA sequences, unique DNA sequences from the capsule loci of C. jejuni, for each Penner type, were identified. The selected genes were further compared to the whole genome sequences of C. jejuni in order to eliminate potential similarities with genes outside the CPS region.

Selection of genes unique to a particular serotype was performed using a local BLAST program. Each single gene of the variable capsule region (between kpsC and kpsF) was compared with a database containing the nucleotides sequences of all the available capsule loci of C. jejuni. The selected genes were further compared to the whole genome sequences of C. jejuni sequenced genomes to eliminate potential similarities with genes outside CPS region.

Figure 2:
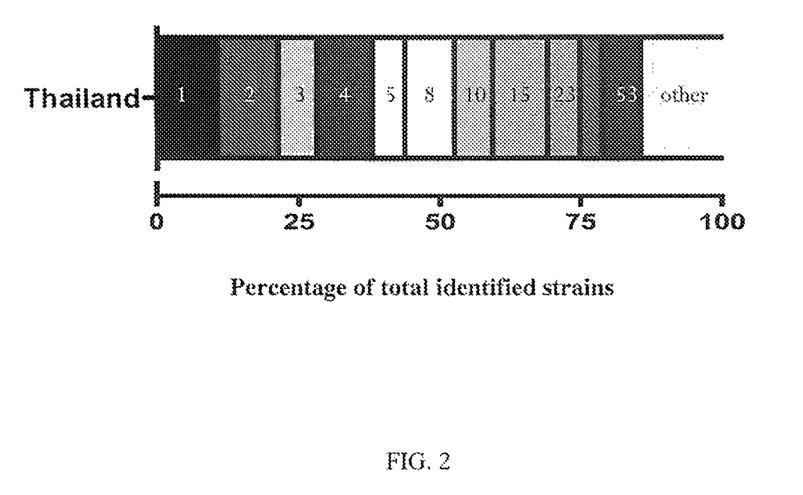
FIG. 2. Graphic depiction illustrating cumulative distribution of C. jejuni serotypes in Thailand (103 strains). Serotypes were determined using Penner serotyping. The numbers in the boxes refer to Penner serotypes.

Penner serotyping was performed on a subset of C. jejuni clinical strains obtained from Thailand. Serotype distribution is shown in FIG. 2. As illustrated in FIG. 2, HS1, 2, 3, 4, 5, 15, 23, 42 and 53 serotypes are the most common serotypes observed in Thailand. These results are in accordance with other Penner serotyping surveys demonstrating that HS1, 2, 3, and especially 4, represent a large percentage of clinical isolates in the world (Asrat, et al. Epidemiol. Infect. 118:222-226 (1997); Jones, et al. J. Infect. 9:51-58 (1984); Karmali et al. J. Infect. Dis. 147:243-246 (1984); Owen, R. J., and J. R. Gibson. PHLS Microbiol. Dig. 12:2-6 (1995); Penner et al., Eur. J. Clin. Microbiol. 2:378-383 (1983)). In addition, some serotypes appear to be more "regional" like HS8 and HS10.

Based on these observations, sequencing of capsule loci of common worldwide and regional Penner serotypes, for which no sequences were available, was performed. CPS locus sequences were obtained by cloning the kpsC-hddA and KpsF-dmhA PCR fragments into a pCR4-TOPO™ vector (Invitrogen, Carlsbad, Calif.) in order to create a representative genomic library. Following purification, clones were sequenced. Assembly was performed using Sequencher® 4.8 (Gene Codes Corporation, Ann Arbor, Mich.). PCR primers were designed to correct errors and close gaps. Development of unique Campylobacter jejuni PCR primer sequences undertaken by sequencing DNA of capsule loci of the strains of HS3; HS3/13/50; HS4; HS8; HS10: HS15; HS17; and HS42, plus HS1/44 and HS44. A summary of the data is presented in Table 1.

TABLE 1

| Penner type | Size (bp) | Accession number | GC (%) | No. Genes | No. MeOPN TF's | Heptose | Deoxy Heptose | CPS structure available (reference) |
|---|---|---|---|---|---|---|---|---|
| HS1 | 15,180 | BX545859[a] | 26.8 | 11 | 1 | No | No | (g) |
| HS2 | 34,180 | AL139078[b] | 26.5 | 28 | 2 | Yes | No | (a) |
| HS3 | 26,371 | HQ343268[f] | 27.3 | 23 | 1 | Yes | Yes | (h) |
| HS3/13/50 | 26,371 | HQ343267[f] | 27.3 | 23 | 1 | Yes | Yes | — |
| HS4 | 22,836 | HQ343269[f] | 28.0 | 18 | 2 | Yes | Yes | — |
| HS4/13/64 | 23,423 | AASY01000000[c] | 28.0 | 18 | 2 | Yes | Yes | (i) |
| HS6 | 26,729 | NC_009839.[d] | 27.6 | 21 | 0 | No | No | (j) |
| HS8 | 22,063 | HQ343270[f] | 27.1 | 18 | 0 | Yes | Yes | — |
| HS10 | 27,307 | HQ343271[f] | 27.1 | 25 | 1 | Yes | Yes | — |
| HS15 | 23,868 | HQ343272[f] | 28.3 | 22 | 1 | Yes | Yes | — |
| HS17 | 22,064 | HQ343273[f] | 27.1 | 18 | 0 | Yes | Yes | — |
| HS19 | 16,727 | BX545860[a] | 26.1 | 13 | 1 | No | No | (k) |
| HS23 | 24,627 | AY332625[a] | 27.0 | 21 | 1 | Yes | Yes | (l; a) |
| HS36 | 24,625 | AY332624[a] | 26.9 | 21 | 1 | Yes | Yes | (l; a) |
| HS23/36 | 24,625 | BX545858[a] | 27.1 | 21 | 1 | Yes | Yes | (l) |
| HS41 | 34,118 | BX545857[a] | 27.2 | 30 | 0 | Yes | Yes | n |
| HS42 | 23,268 | HQ343274[f] | 26.9 | 21 | 0 | Yes | Yes | — |
| HS53 | 18,272 | CP000025.1[e] | 27.0 | 15 | 0 | Yes | Yes | (m) |

[a] Karlyshev, et al., Mol. Microbiol., 55: 90-103 (2005)
[b] Parkhill, et al., Nature 403: 665-668 (2000)
[c] Poly, et al., Infect. Immun., 75: 3425-3433 (2007)
[d] Pearson, et al., J. Bacteriol., 189: 8402-8403 (2007)
[e] Fouts, et al., PLoS. Biol., 3: e15 (2005)
[f] Current study
[g] McNall, et al., FEBS J. 272: 4407-4422 (2005)
[h] Aspinall, et al., Eur. J. Biochem. 231: 570-578 (1995)
[i] Chen, et al., Carbohydr. Res. 343: 1034-1040 (2008)
[j] Muldoon, et al., Carbohydr. Res. 337: 2223-2229 (2002)
[k] McNally, et al., FEBS J. 273: 3975-3989 (2006)
[l] Aspinall, et al., Carbohydr. Res. 231: 13-30 (1992)
[m] Gilbert, et al., Chembiochem. 8: 625-631 (2007)
[n] Hannify, et al., Carbohydr. Res. 319: 124-132 (1999)

The capsule loci sequences obtained were then compared to Penner serotyping results. The results of this comparison led to corroboration of complexes in the Penner serotyping system. For example, Karlyshev et al., Mol. Microbiology, 55(1): 90-103, determined that strains in the HS23/36 complex (i.e. HS23, HS36 and HS23/36) have the same CPS loci. Mu_HS23 primers identify strain that belong to the HS23/36 complex (including: HS23, HS36 and HS23/36).

HS1 is often found in complex with HS44. However, no differences in capsule sequence were observed between the HS1 type strain and a clinical isolate that typed as HS1/44. Interestingly, the sequence of the HS44 type strain appeared to be drastically different than HS1 or HS1/44 strains. For these reasons primers Mu_HS1 D recognize HS1 as well as HS1/44 (HS1 complex) strains, but not HS44 strains. A primer set Mu_HS44 was specifically designed to recognize this serotype. HS8 and HS17 are also often associated. No difference of capsule sequence was identified between these serotypes.

Furthermore, HS8 and HS17 are often associated. Mu_HS17 primers identify both HS8, HS17 and HS8/17 strains (defined as the HS8 complex). Similarly, the HS4 serotype is often associated with HS13, HS43, HS50, HS64 or HS65. Sequencing of three strains belonging to this complex (HS4, HS13 and HS4/13/64) allowed discrimination of these strains into two groups based on their capsule loci. Primer sets were designed to distinguish these groups: Mu_HS4B that recognized HS4, HS13 type strains, as well as some strains typed as HS4/13/64. Un_8486 primers identified strains belonging to HS4/13/64 complexes as well as the HS64 type strain.

A database containing all available CPS loci was created to identify unique regions of each serotype. This data set included a partial sequence of the type strain of HS44, which forms a complex with HS1. In one embodiment, two primer sets were designed for the HS4 complex. These are based on differences in MeOPN transferases among the sequenced strains in this complex. The embodiment is based on an assumption that the differences among the HS4 complex are due to differences in the position of MeOPN on the polysaccharide. These primer sets, named Mu_HS4 and Mu_8486, respectively, were designed in HS4.07 and Cj8486_1475, both putative MeOPN transferases. Since some HS4 strains contain two MeOPN transferases, a strain can theoretically be positive with both Mu_8486 and Mu_HS4. Since the CPS loci of HS8 and HS17 are so similar, a single primer set was designed for this complex. Although CPS has been shown not to be the serodeterminant of the HS6 serotype, the CPS genes in this strain do not match any of the other published sequences so a primer set was designed for this CPS type as well.

EXAMPLE 2

Design of Multiplex PCR Assay to Penner Serotypes

In a preferred embodiment, PCR primers were designed in regions that were found unique to each particular *C. jejuni* serotype. In one embodiment, primer sets are grouped into two 'mixes' based on the sizes of the products (Table 2). The alpha mix contains primers that distinguish HS2, the HS3 complex, HS6, HS10, HS15, HS41, HS53 and part of the HS4 complex (HS4 and HS13, termed HS4A). The beta mix contains primers that distinguish the HS1 complex (including HS1 and HS1/44), the HS23/36 complex, the HS8 complex (HS8 and HS17), HS42, HS44 and part of the HS4 complex (HS4/13/64 or CG8486-like, termed HS4B).

In a preferred embodiment, the PCR primers were designed to permit multiplex PCR. Multiplex PCR significantly reduces the number of reactions needed for strain identification. Design of the multiplex primers was conducted utilizing the online software MuPlex™ (Boston University, Boston, Mass.) (described in Rachlin, et al., Nucleic Acid Research 33 (Web Server Issue): W544-W547) (2005).

Primers were designed with the following parameters: length between 18 and 30 residues, 20 to 50% GC, Tm ranging from 57° to 63° C. with a minimum product difference of 20 bp. The primer sequences were verified for absence of dimerization or hairpin formation using AutoDimer™ (Vallone and Butler, Biotechniques 37(2): 226-231 (2004)).

Primers were evaluated for their ability to enable efficient amplification of predicted product and for not interfering with other primers, capable of amplifying *Campylobacter jejuni* DNA, included in the reaction. The primer sets were designed to produce amplicons that differ by at least 20 bp from the other amplicons in the same mix. Primer sets were judged satisfactory if they produced the expected size PCR product on their Penner serotype DNA template or related complexes and were negative for other tested serotypes. Shown in Table 2 are the strains identified by each primer pair, and the product size, as well as the associated SEQ ID Number.

d. Subsequent to PCR amplification compare PCR product size.

Amplifying DNA from an unknown *C. jejuni* sample, using the primers in Table 2, and comparing the size of the ensuing amplification products permits identification of 17 *C. jejuni* Penner serotypes (14 CPS types). In a preferred embodiment, the amplified DNA is separated and sized through an agarose gel (2%), run in 0.5×TBE buffer. The sizes of the PCR products and corresponding serotype are determined by comparison with 100 bp molecular size standards. Although agarose gel electrophoresis is a preferred method, other methods to analyze PCR product size are contemplated.

In other embodiments, methods are carried out, at least in part, using a solid support. A variety of different supports can be used. In some embodiments, the solid support is a single solid support, such as a chip or wafer, or the interior or exterior surface of a tube, cone, plastic plate or other article. In some embodiments, the solid support is a particulate support, also referred to as a microsphere, bead or particle. Typically, the particles form groups in which particles within each group have a particular characteristic. Examples of suitable characteristics include, but are not limited to, color, fluorescence frequency, density, size, or shape. The selection of characteristics will depend on multiple criteria including the ability to distinguish or separate target-bound particles from particles of other groups. Particles can be separated by a

TABLE 2

Alpha mix PCR multiplex primers

| | Product Size (bp) | Penner type recognized | Designed in Gene | Forward sequence (SEQ ID No.) | Reverse sequence (SEQ ID No.) | Product (SEQ ID No.) |
|---|---|---|---|---|---|---|
| Mix Alpha | | | | | | |
| Mu_HS2 | 62 | HS2 | Cj1437c | 1 | 2 | 29 |
| Mu_HS3 | 149 | HS3 | HS3.17 | 3 | 4 | 30 |
| Mu_HS4 | 370 | HS4A | HS4.07 | 5 | 6 | 31 |
| Mu_HS6 | 185 | HS6 | C8J_1331 | 7 | 8 | 32 |
| Mu_HS10 | 229 | HS10 | HS10.08 | 9 | 10 | 33 |
| Mu_HS15C | 325 | HS15 and HS31 | HS15.12 | 11 | 12 | 34 |
| Mu_HS41 | 279 | HS41 | HS41.22c | 13 | 14 | 35 |
| Mu_HS53 | 251 | HS53 | CJE1602 | 15 | 16 | 36 |
| Mix Beta | | | | | | |
| Mu_HS1D | 607 | HS1 complex | HS1.08 | 17 | 18 | 37 |
| Mu_HS17 | 342 | HS8 and HS17 | HS17.16 | 19 | 20 | 38 |
| Mu_8486 | 652 | HS4 B | Cj8486_1475 | 21 | 22 | 39 |
| Mu_HS23 | 161 | HS23/36 | CJJ81176_1435 | 23 | 24 | 40 |
| Mu_HS42E | 441 | HS42 | HS42.14 | 25 | 26 | 41 |
| Mu_HS44 | 148 | HS44 | Not annotated | 27 | 28 | 42 |

Although other potential parameters are possible, multiplex PCR amplification conditions are standardized for primers in the alpha and beta mixes. A preferred embodiment of the PCR identification method comprises the following steps:
 a. Obtain a sample suspected of containing *Campylobacter jejuni* DNA;
 b. Subject sample containing said DNA to one or more primer pairs listed in Table 2, or a primer pair with capable of amplifying the same product shown in Table 2. In a preferred embodiment, the primers are 18-30 nucleotides, have a G/C content of 20-50%, and a melting temperature between about 57° C. and 63° C.;
 c. Amplify target DNA under the following parameters: 94° C. for 30", 56° C. for 30", 72° C. for 45" for a total of 29 cycles;

number of methods. In a preferred embodiment, the particles can be separated using techniques, such as, for example, flow cytometry.

The particles can be fabricated from virtually any insoluble or solid material. For example, the particles can be fabricated from silica gel, glass, nylon, resins, Sephadex™, Sepharose™, cellulose, magnetic material, a metal (e.g., steel, gold, silver, aluminum, copper, or an alloy) or metal-coated material, a plastic material (e.g., polyethylene, polypropylene, polyimide, polyester, polyvinylidenefluoride (PVDF)) and the like, and combinations thereof. Examples of suitable micro-beads are described, for example, in U.S. Pat. Nos. 5,736,330, 6,046,807 and 6,057,107, all of which are incorporated herein by reference in their entirety.

Thus, in one embodiment, the multiplex method described herein is performed using microspheres conjugated to unique capture oligonucleotides, permitting the analysis of many different nucleic acids in a single reaction. Each unique capture oligonucleotide is complementary to a unique tag sequence within one of the amplicons to be detected. In this embodiment, the microsphere mix consists of a number of microspheres equal to the number of serotypes that can be detected in the assay. Each of the microspheres contains a different fluorescent dye mix and is coupled to a unique capture oligonucleotide sequence complementary to a unique tag sequence within the amplicon of each serotype of interest. The hybridization of the capture oligonucleotide and the tag sequence of an amplicon results in the coupling of the amplicon to the solid support. The unique capture oligonucleotide and its complementary tag sequence are, thus, associated with a single, specific Penner serotype. The capture oligonucleotides are designed so there is no cross-hybridization between the capture oligonucleotides and the amplicons from more than one serotype under the hybridization conditions used.

In this method, the multiplex Alpha and Beta primer sets are used to amplify regions of interest in a *C. jejuni* DNA sample in the presence of a biotinylated dNTP mixture. Instead of running the amplified PCR fragments on an agarose gel to estimate their size, the amplified PCR fragments are incubated with microspheres conjugated to capture oligonucleotides specific for the serotypes of interest and streptavidin conjugated to a dye, such as phycoerythrin, and analyzed using an appropriate detection system.

EXAMPLE 3

Comparison/Validation of Multiplex PCR Method to Penner Serotyping

From the correlations observed between Penner serotyping data and capsule loci sequence information, PCR primers were developed that were specific to available CPS strains. The primers were then validated against species of DNA of from *C. jejuni* strains of known Penner serotypes.

Validation of the inventive multiplex PCR assay method was conducted on 244 strains from Thailand and Egypt that had been Penner serotyped in reference laboratories. The result of this study is illustrated in Table 3.

In summary, the multiplex method had a specificity and accuracy of >97% and a sensitivity of >89%. The method detected 100% of strains of HS2 (30/30), HS8/17 (10/10), HS15 (19/19), HS23/36 (13/13), HS41 (2/2), HS53 (16/16) and HS6 (1/1). There were two false negatives with the HS1/44 primers (2/25), the HS3 complex primers (2/25), and the HS4 complex primers (2/20). The HS10 primers resulted in one false negative (1/14) and two false positives (one HS1/44 and one HS44 serotype). The HS6 primers picked up five strains, two of which belonged to the HS3 complex, and the HS15 primers picked up 6 false positives, all of which were HS31. Since there is no information about the CPS locus or structure of HS31, this may suggest a relationship between HS15 and HS31, although they are not part of a complex. Included within the 244 strains were 37 strains that belonged to 15 serotypes not included in the multiplex. A total of 27 of these 37 strains were negative with the multiplex primers, but six HS31 strains reacted with the HS15 primers, as discussed above, individual strains that typed as HS32, HS35 and HS59 reacted with the HS6 primers, and one HS37 strain reacted with the HS3 primers. There were also 23 strains that were not able to be typed in the Penner scheme, and 8 of these reacted with the HS6 primers, two reacted with the HS15 primers, and one each reacted with HS2 and HS10 primers. These data suggest that some strains are not able to be typed in the Penner scheme because CPS is not expressed.

TABLE 3

| Primer set | # strains | True positive | False Positive | False negative | True Negative | % Accuracy[1] | % Sensitivity[2] | % Specificity[3] |
|---|---|---|---|---|---|---|---|---|
| HS1/44 Complex | 25 | 23 | 0 | 2 | 219 | 99.18 | 92.00 | 100.00 |
| HS2 | 30 | 30 | 0 | 0 | 214 | 100.00 | 100.00 | 100.00 |
| HS3 Complex | 26 | 24 | 1 | 2 | 217 | 98.77 | 92.31 | 99.54 |
| HS4 Complex | 20 | 18 | 0 | 2 | 224 | 99.18 | 90.00 | 100.00 |
| HS6 | 1 | 1 | 5 | 0 | 238 | 97.95 | 100.00 | 97.94 |
| HS8/17 complex | 10 | 10 | 0 | 0 | 234 | 100 | 100.00 | 100 |
| HS10 | 14 | 13 | 2 | 1 | 228 | 98.77 | 92.86 | 99.13 |
| HS15 | 19 | 19 | 6 | 0 | 219 | 97.54 | 100.00 | 97.33 |
| HS23/36 complex | 13 | 13 | 1 | 0 | 230 | 99.59 | 100.00 | 99.57 |
| HS41 | 2 | 2 | 0 | 0 | 242 | 100.00 | 100.00 | 100.00 |
| HS42 | 8 | 8 | 0 | 0 | 236 | 100.00 | 100.00 | 100.00 |
| HS53 | 16 | 16 | 1 | 0 | 227 | 99.59 | 100.00 | 99.56 |

[1]Accuracy = (true positive + true negative)/true positive + true negative + false positive + false negative)
[2]Sensitivity = true positive/(true positive + false negative)
[3]Specificity = true negative/(true negative + false positive)

Having described the invention, one of skill in the art will appreciate in the appended claims that many modifications and variations of the present invention are possible in light of the above teachings. It is therefore, to be understood that, within the scope of the appended claims, the invention may be practices otherwise than as specifically described.

What is claimed is:

1. A method of identifying *Campylobacter jejuni* strains in a sample suspected of containing *Campylobacter jejuni* DNA by polymerase chain reaction, wherein the amplification products of said polymerase chain reaction are derived from genes within the *Campylobacter jejuni* polysaccharide capsule (CPS) loci, comprising: (a) subjecting DNA from said sample to a PCR amplification reaction using one or more PCR primer pairs targeting one or more regions of the O-methyl phosphoramidate synthesis region, heptose synthesis and hyper-variable region of the polysaccharide capsule loci of *Camplylobacter jejuni*; (b) analyzing amplification products resulting from said amplification reaction.

2. The method of claim 1, wherein said polysaccharide capsule loci is derived from *Campylobacter jejuni* strains selected from HS2; HS3; HS6; HS10; HS15C; HS41; HS53; HS1; HS23; HS42; HS44; HS17 and strain 8486.

3. The method of claim 2, wherein said HS2 PCR primers recognize HS2 Penner type; HS3 PCR primers recognize H3 Penner type; HS4 PCR primers recognize HS4 A Penner complex; HS6 PCR primers recognize HS6 Penner type; HS 10 PCR primers recognize HS10 Penner type; HS15C PCR primers recognize HS15 and HS31 Penner types; HS41 PCR primers recognize HS41 Penner type; HS53 PCR primers recognize HS53 Penner type; HS1D PCR primers recognize HS1 complex Penner type; HS17 PCR primers recognize HS8 and HS17 Penner type; 8486 PCR primers recognize HS4B Penner type; HS23 PCR primers recognize HS23 Penner complex; HS42E PCR primers recognize HS42 Penner type; HS44 PCR primers recognize HS44 Penner type.

4. The method of claim 1, wherein said amplification products are analyzed by size determination.

5. The method of claim 4, wherein the amplification of products are analyzed by agarose gel electrophoresis.

6. The method of claim 1, wherein said PCR primer pairs contain sequences selected from the group consisting of: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16; SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO 27 and SEQ ID NO: 28.

7. The method of claim 1, wherein said PCR reaction is multiplex amplification reaction.

8. The method of claim 7, wherein said PCR primer pairs are grouped into an alpha mix comprising one or more sequence pairs selected from the group consisting of: SEQ ID NO: 1 and SEQ ID NO: 2; SEQ ID NO: 3 and SEQ ID NO: 4; SEQ ID NO: 5 and SEQ ID NO: 6; SEQ ID NO: 7 and SEQ ID NO: 8; SEQ ID NO: 9 and SEQ ID NO: 10; SEQ ID NO: 11 and SEQ ID NO: 12; SEQ ID NO: 13 and SEQ ID NO: 14; SEQ ID NO: 15 and SEQ ID NO: 16, and a beta mix comprising one or more sequence pairs selected from the group consisting of: SEQ ID NO: 17 and SEQ ID NO: 18; SEQ ID NO: 19 and SEQ ID NO: 20; SEQ ID NO: 21 and SEQ ID NO: 22; SEQ ID NO: 23 and SEQ ID NO: 24; SEQ ID NO: 25 and SEQ ID NO: 26; SEQ ID NO 27 and SEQ ID NO: 28.

9. The method of claim 1, wherein said primer pairs are grouped in order to discriminate PCR amplification reaction product sizes.

10. The method of claim 1, wherein said sample is a clinical sample.

11. The method of claim 1, wherein said sample is collected from a matrix selected from the group consisting of a bacterial culture, a blood, a tissue, and fecal material.

12. The method of claim 1, wherein the primers have about 18-30 nucleotides, a G/C content of 20-50%, and a melting temperature between about 57° C. and 63° C.

13. The method of claim 1, wherein said amplification reaction yields one or more of amplification products selected from the group consisting of SEQ ID NO: 29; SEQ ID NO: 30; SEQ ID NO: 31; SEQ ID NO: 32; SEQ ID NO: 33; SEQ ID NO: 34; SEQ ID NO: 35; SEQ ID NO: 36; SEQ ID NO: 37; SEQ ID NO: 38; SEQ ID NO: 39; SEQ ID NO: 40; SEQ ID NO: 41; and SEQ ID NO: 42.

* * * * *